United States Patent
Pollard et al.

(10) Patent No.: US 10,358,679 B2
(45) Date of Patent: Jul. 23, 2019

(54) MICRORNA BIOMARKERS FOR POSTTRAUMATIC STRESS DISORDER AND METHODS OF USE THEREOF

(71) Applicant: The Henry M. Jackson Foundation for the Advancement of Military Medicine, Inc., Bethesda, MD (US)

(72) Inventors: Harvey B. Pollard, Potomac, MD (US); Roopa Biswas, Bethesda, MD (US)

(73) Assignee: The Henry M. Jackson Foundation for the Advancement of Military Medicine, Inc., Bethesda, MD (US)

(*) Notice: Subject to any disclaimer, the term of this patent is extended or adjusted under 35 U.S.C. 154(b) by 0 days.

(21) Appl. No.: 15/514,175

(22) PCT Filed: Sep. 25, 2015

(86) PCT No.: PCT/US2015/052178
§ 371 (c)(1),
(2) Date: Mar. 24, 2017

(87) PCT Pub. No.: WO2016/049429
PCT Pub. Date: Mar. 31, 2016

(65) Prior Publication Data
US 2017/0247761 A1 Aug. 31, 2017

Related U.S. Application Data

(60) Provisional application No. 62/055,934, filed on Sep. 26, 2014.

(51) Int. Cl.
C12N 15/113 (2010.01)
C12Q 1/6883 (2018.01)

(52) U.S. Cl.
CPC .......... *C12Q 1/6883* (2013.01); *C12N 15/113* (2013.01); *C12N 2310/141* (2013.01); *C12Q 2600/118* (2013.01); *C12Q 2600/158* (2013.01); *C12Q 2600/178* (2013.01)

(58) Field of Classification Search
CPC ................ C12N 15/113; C12Q 1/6883; C12Q 2600/178
See application file for complete search history.

(56) References Cited

FOREIGN PATENT DOCUMENTS

WO 2015/164431 A2 10/2015

OTHER PUBLICATIONS

Carlsen et al. (Arthritis and Rheumatism (May 2013) vol. 65(5):1324-1334). (Year: 2013).*
Wingo et al., DICER1 and microRNA regulation in post-traumatic stress disorder with comorbid depression, Nature Communications, 6: 10106 (2015).
Zhou et al., Dysregulation in microRNA Expression Is Associated with Alterations in Immune Functions in Combat Veterans with Post-Traumatic Stress Disorder, Plos One, 9: e94075 (2014).
Balakathiresan et al., MicroRNA Let-7i Is a Promising Serum Biomarker for Blast-Induced Traumatic Brain Injury, Journal of Neurotrauma, 29: 1379-1387 (2012).
Balakathiresan et al., Serum and amygdala microRNA signatures of posttraumatic stress: Fear correlation and biomarker potential, Journal of Psychiatric Research, 57: 65-73 (2014).
Lei et al., Microarray based analysis of microRNA expression in rat cerebral cortex after traumatic brain injury, Brain Research, 1284: 191-201 (2009).
Smalheiser et al., MicroRNA Expression Is Down-Regulated and Reopranized in Prefrontal Cortex of Depressed Suicide Subjects, Plos One, 7: e33201 (2012).
Smalheiser et al., Expression of microRNA's and Other Small RNAs in Prefrontal Cortex in Schizophrenia, Bipolar Disorder and Depressed Subjects, Plos One, 9: e86469 (2014).
Extended European search report issued in corresponding European Application No. 15844087.5 dated May 9, 2018.

* cited by examiner

*Primary Examiner* — J. E. Angell
(74) *Attorney, Agent, or Firm* — Morgan, Lewis & Bockius LLP

(57) ABSTRACT

Methods of detecting or diagnosing posttraumatic stress disorder (PTSD) in a human subject are disclosed. In addition, methods of monitoring the progression of PTSD in a human subject, methods of treating a patient with PTSD, kits for diagnosing PTSD in a human subject suspected of having PTSD, and methods of detecting a microRA (miRNA) or plurality of miRNAs in a biological sample from a human subject are also disclosed.

14 Claims, 1 Drawing Sheet
Specification includes a Sequence Listing.

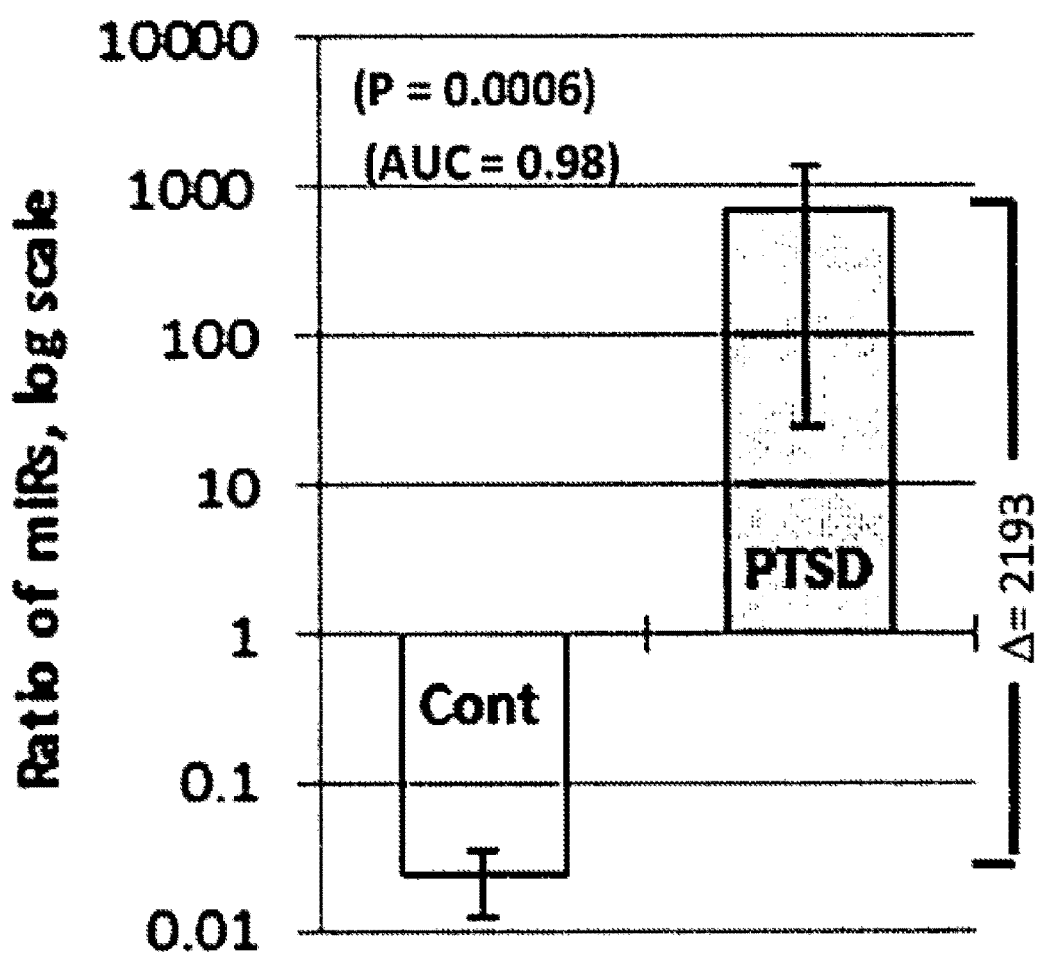

SEQUENCE LISTING

```
<160> NUMBER OF SEQ ID NOS: 14

<210> SEQ ID NO 1
<211> LENGTH: 23
<212> TYPE: RNA
<213> ORGANISM: Homo sapiens

<400> SEQUENCE: 1
uguaguguuu ccuacuuuau gga                                          23

<210> SEQ ID NO 2
<211> LENGTH: 21
<212> TYPE: RNA
<213> ORGANISM: Homo sapiens

<400> SEQUENCE: 2
aaagcgcuuc ccuucagagu g                                            21

<210> SEQ ID NO 3
<211> LENGTH: 23
<212> TYPE: RNA
<213> ORGANISM: Homo sapiens

<400> SEQUENCE: 3
aacauucaac gcugucggug agu                                          23

<210> SEQ ID NO 4
<211> LENGTH: 23
<212> TYPE: RNA
<213> ORGANISM: Homo sapiens

<400> SEQUENCE: 4
```

-continued

```
uaaagugcuu auagugcagg uag                                        23

<210> SEQ ID NO 5
<211> LENGTH: 23
<212> TYPE: RNA
<213> ORGANISM: Homo sapiens

<400> SEQUENCE: 5
ugagguuggu guacugugug uga                                        23

<210> SEQ ID NO 6
<211> LENGTH: 22
<212> TYPE: RNA
<213> ORGANISM: Homo sapiens

<400> SEQUENCE: 6
uagcaccauc ugaaaucggu ua                                         22

<210> SEQ ID NO 7
<211> LENGTH: 22
<212> TYPE: RNA
<213> ORGANISM: Homo sapiens

<400> SEQUENCE: 7
cagugcaaug uuaaaagggc au                                         22

<210> SEQ ID NO 8
<211> LENGTH: 22
<212> TYPE: RNA
<213> ORGANISM: Homo sapiens

<400> SEQUENCE: 8
uagcaccauu ugaaaucggu ua                                         22

<210> SEQ ID NO 9
<211> LENGTH: 22
<212> TYPE: RNA
<213> ORGANISM: Homo sapiens

<400> SEQUENCE: 9
cucaguagcc aguguagauc cu                                         22

<210> SEQ ID NO 10
<211> LENGTH: 22
<212> TYPE: RNA
<213> ORGANISM: Homo sapiens

<400> SEQUENCE: 10
ucaggcucag uccccucccg au                                         22

<210> SEQ ID NO 11
<211> LENGTH: 22
<212> TYPE: RNA
<213> ORGANISM: Homo sapiens

<400> SEQUENCE: 11
uacggugagc cugucauuau uc                                         22

<210> SEQ ID NO 12
<211> LENGTH: 21
<212> TYPE: RNA
<213> ORGANISM: Homo sapiens

<400> SEQUENCE: 12
```

```
gaacggcuuc auacaggagu u                                                    21

<210> SEQ ID NO 13
<211> LENGTH: 22
<212> TYPE: RNA
<213> ORGANISM: Homo sapiens

<400> SEQUENCE: 13
uccuguacug agcugccccg ag                                                   22

<210> SEQ ID NO 14
<211> LENGTH: 21
<212> TYPE: RNA
<213> ORGANISM: Homo sapiens

<400> SEQUENCE: 14
gaaagcgcuu cucuuuagag g                                                    21
```

MICRORNA BIOMARKERS FOR POSTTRAUMATIC STRESS DISORDER AND METHODS OF USE THEREOF

STATEMENT REGARDING FEDERALLY SPONSORED RESEARCH OR DEVELOPMENT

The invention was made with government support under grant W81XWH-08-2-0201 awarded by the United States Army Medical Research and Materiel Command. The government has certain rights in the invention.

REFERENCE TO SEQUENCE LISTING

A computer readable text file, entitled "044508-5053-WO-SequenceListing.txt," created on or about Sep. 25, 2015 with a file size of about 3 kb contains the sequence listing for this application and is hereby incorporated by reference in its entirety.

FIELD OF THE INVENTION

The present disclosure relates to methods of detecting or diagnosing posttraumatic stress disorder (PTSD) in a human subject. The present disclosure also relates to methods of monitoring the progression of PTSD in a human subject, methods of treating a patient with PTSD, a kit for diagnosing PTSD in a human subject suspected of having PTSD, and methods of detecting a microRNA (miRNA) or plurality of miRNAs in a biological sample from a human subject.

BACKGROUND OF THE INVENTION

Post-traumatic stress disorder (PTSD) is psychiatric disorder, which occurs following exposure to traumatic events. PTSD may be acute or chronic, and can have a waxing and waning course of symptoms that can persist for months, years or decades (Diagnostic and Statistical Manual of Mental Disorders-V (DSM-V), and www.behavenet.com/capsules/disorders/ptsd.htm). The diagnosis is principally clinical, based on the fact that something bad happened, and that the patient was there. Behaviorally, the PTSD patient exhibits three defined symptom clusters: (i) hyperarousal (including hypervigilence, irritability, and heightened startle reaction), (ii) avoidance of the condition that was associated with the precipitating event; and (iii) mental re-experiencing of the precipitating event, as if it were actually happening again and again.

There is increasing evidence that there are predisposing genetic risk factors contributing to the development of PTSD. The predisposing deficits are associated behaviorally with hyperarousal, and functionally with increased activity in the amygdala and dorsal anterior cingulate cortex ibid. Evidence from studies with twins suggest that the predisposing deficits are modestly heritable (H), with probabilistic H values of 30-70%. Consistent results have also come from comprehensive studies of soldiers in the Israeli Defense Forces, who were imaged and analyzed before and after front line combat.

The genetic bases of this heritable predisposition are only just beginning to be discerned. Presently, 20 different sequence polymorphisms have been considered as contributing to the predisposing risk factor. Of these, three types of mutations are being principally studied in parallel with functional changes in brains of patients with PTSD. These include (i) catechol-O-methyl transferase; (ii) polymorphisms in the serotonin transporter SLC6A4 gene (viz, the short allele [5HTTLPRs]); and (iii) regulation of glucocorticoid receptor activation by FKBP5 by allele-specific demethylation. However, how these mutations correlate with structural and functional changes in the brain are not known.

The acquired defects following trauma are associated with loss of control on re-experiencing and avoidance behavior. These losses are functionally paralleled by reduced activity in the ventromedial prefrontal cortex (vmPFC, "Area 25"), and reduced activity and volume in the hippocampus. The present thinking is that traumatic experience is responsible for (i) suppressing activity in area 25; (ii) reducing the size of the hippocampus; and (iii) interfering with communication between area 25 and the hippocampus though the connecting entorhinal cortex and uncinate fasciculus.

SUMMARY OF THE INVENTION

In one aspect, the present disclosure relates to methods of detecting or diagnosing posttraumatic stress disorder (PTSD) in a human subject, the method comprising: (a) determining levels of one or more micro RNA (miRNA) in a biological sample taken from the human subject, and (b) comparing the determined levels of the one or more miRNA against levels of the same one or more miRNA from human subjects determined not to be suffering from PTSD, wherein an increase or decrease in the levels of the one or more miRNA compared to levels of the one or more miRNA from human subjects determined not to be suffering from PTSD is indicative that the human subject may be suffering from PTSD.

In another aspect, the present disclosure also relates to methods of monitoring the progression of post traumatic stress disorder (PTSD) in a human subject, the method comprising: (a) analyzing at least two samples from the human subject with each sample taken at different time points to determine the levels of one or more specific micro RNA (miRNA), and (b) comparing the levels of the one or more specific miRNA, over time to determine if the human subject's levels of the one or more specific miRNA is changing over time, wherein a change in the human subject's levels of the one or more specific miRNA over time is indicative that the human subject's risk of suffering from PTSD is increasing over time.

In another aspect, the present disclosure also relates to methods of detecting or diagnosing post traumatic stress disorder (PTSD) in a human subject suspected of having PTSD, the method comprising: (a) quantifying levels of expression of one or more micro RNA (miRNA) in a first sample derived from the human subject, (b) quantifying levels of expression of the same one or more miRNA in a second sample derived from a body fluid obtained from human subjects determined not to be suffering from PTSD, and (c) comparing the quantified levels of expression the one or more miRNA from the first sample with the levels of expression from the second sample. In one embodiment, wherein detecting or diagnosing PTSD is achieved when there is increased or decreased levels of expression of the miRNA in the first sample compared with the second sample. In one embodiment, the levels of expression are quantified by real-time PCR and the increased or decreased levels of expression are evaluated by having a p value of less than 0.05 in a statistical test.

In another aspect, the present disclosure also relates to methods of detecting or diagnosing post traumatic stress disorder (PTSD) in a human subject, the method comprising: (a) determining levels of a first micro RNA (miRNA) and a second miRNA in a biological sample taken from the human subject, (b) calculating the ratio of the determined levels of the first miRNA versus the second miRNA, and (c) comparing the calculated ratio for the sample from the human subject against ratio of the same first and second miRNA from human subjects determined not to be suffering from PTSD, wherein an increase or decrease in the ratio for the sample from the human subject against ratio of the same first and second miRNA from human subjects determined not to be suffering from PTSD is indicative that the human subject may be suffering from PTSD.

In one aspect, the present disclosure also relates to a process for treating a patient suspected of having PTSD, the process comprising: (a) detecting or diagnosing the patient by determining the levels of one or more miRNA from the patient and comparing the levels of the one or more miRNA against levels of the same miRNA from human subjects not suffering from PTSD; and administering a therapeutic or behavioral treatment for PTSD to the patient, wherein said therapeutic or behavioral treatment is the administration of selective serotonin reuptake inhibitors (SSRI's), cognitive behavior therapy (CBT), administration of a microRNA mimic of at least one measured miRNA, administration of a microRNA inhibitor of at least one measured miRNA, administration of an anti-depressant, or combinations thereof.

In one aspect, the miRNA that is analyzed and used in the methods and kits of the present invention is any of miR-142-3p, miR-518e, miR-181a, miR-20a, miR-672, miR-29a, miR-130a, miR-29c, miR-220, miR-484, miR-433, miR-337-5p, miR-486-5p, and miR-518f-3p.

In another aspect, the levels of one or more specific micro RNA are determined by a real time PCR. The methods of detecting or diagnosing the PTSD according to some embodiments of the present specification further comprise amplifying the miRNA.

In another aspect, the present disclosure is related to a kit for detecting or diagnosing post traumatic stress disorder (PTSD) in a human subject suspected of having PTSD, the kit comprising: one or more polynucleotide molecules that hybridize to one or more miRNAs selected from the group consisting of miR-142-3p, miR-518e, miR-181a, miR-20a, miR-672, miR-29a, miR-130a, miR-29c, miR-220, miR-484, miR-433, miR-337-5p, miR-486-5p, and miR-518f-3p, wherein the polynucleotide molecules are labeled or immobilized on a solid substrate.

In another aspect, the present disclosure is related to a method of detecting an miRNA or plurality of miRNAs in a biological sample, comprising: contacting a first biological sample from a subject suspected of having a PTSD with a probe for binding at least one miRNA selected from the group consisting of miR-142-3p, miR-518e, miR-181a, miR-20a, miR-672, miR-29a, miR-130a, miR-29c, miR-220, miR-484, miR-433, miR-337-5p, miR-486-5p, and miR-518f-3p, to produce an miRNA-probe complex; and detecting with Northern Blot Analysis or a real-time PCR the presence or absence of the miRNA-probe complex, wherein the absence of the miRNA-probe complex is indicative of the absence of the microRNA in the first biological sample.

BRIEF DESCRIPTION OF THE DRAWINGS

FIG. 1 shows that the ratio of miR-181a/nniR-337-5p distinguishes PTSD from Healthy Control 9 AM plasma with high range and significance. Range is 2193. P=0.0006; AUC=0.98.

DETAILED DESCRIPTION OF THE INVENTION

The present invention relates to microRNA (miRNA) biomarkers from subjects with posttraumatic stress disorder (PTSD), and their use thereof. miRNA are small RNA molecules (e.g. 22 nucleotides long) and are often, but need not be, post-transcriptional regulators that bind to complementary sequences on target messenger RNA transcripts (mRNA), usually resulting in translational repression and gene silencing. MiRNA may serve as good biomarkers because they are highly stable in serum due to their ability to withstand repeated freeze thaw, enzymatic degradation, and extreme pH conditions. As used herein, the term "microRNA" (miRNA) includes human miRNA, mature single stranded miRNA, precursor miRNA (pre-miR), and variants thereof, which may be naturally occurring. In some instances, the term "miRNA" also includes primary miRNA transcripts and duplex miRNA. Unless otherwise noted, as used herein, the name of a specific miRNA refers to the mature miRNA. For example, miR-194 refers to a mature miRNA sequence derived from pre-miR-194. The sequences for particular miRNA, including human mature and precursor sequences, are reported, for example, in miRBase: Sequences Database on the web at mirbase.org (version 21 released June 2014); Griffiths-Jones, Nucleic Acids Research (2008) 36, Database Issue, D154-D158; Griffiths-Jones, Nucleic Acids Research (2006) 34, Database Issue, D140-D144; Griffiths-Jones, Nucleic Acids Research, (2004) 32, Database Issue, D109-D111). For certain miRNA, a single precursor contains more than one mature miRNA sequence. In other instances, multiple precursor miRNA contain the same mature sequence. In some instances, mature miRNA have been re-named based on new scientific consensus. The skilled artisan will appreciate that scientific consensus regarding the precise nucleic acid sequence for a given miRNA, in particular for mature forms of the miRNA, may change with time.

In another aspect, the present disclosure relates to methods of detecting or diagnosing posttraumatic stress disorder (PTSD) in a human subject, the method comprising: (a) determining levels of one or more micro RNA (miRNA) in a biological sample taken from the human subject, and (b) comparing the determined levels of the one or more miRNA against levels of the same one or more miRNA from human subjects determined not to be suffering from PTSD, wherein an increase or decrease in the levels of the one or more miRNA compared to levels of the one or more miRNA from human subjects determined not to be suffering from PTSD is indicative that the human subject may be suffering from PTSD.

In another aspect, the present disclosure also relates to methods of monitoring the progression of post traumatic stress disorder (PTSD) in a human subject, the method comprising: (a) analyzing at least two samples from the human subject with each sample taken at different time points to determine the levels of one or more specific micro RNA (miRNA), and (b) comparing the levels of the one or more specific miRNA, over time to determine if the human subject's levels of the one or more specific miRNA is changing over time, wherein a change in the human subject's levels of the one or more specific miRNA over time is indicative that the human subject's risk of suffering from PTSD is increasing over time.

In another aspect, the present disclosure also relates to methods of detecting or diagnosing post traumatic stress disorder (PTSD) in a human subject, the method comprising: (a) determining levels of a first micro RNA (miRNA) and a second miRNA in a biological sample taken from the human subject, (b) calculating the ratio of the determined levels of the first miRNA versus the second miRNA, and (c) comparing the calculated ratio for the sample from the human subject against ratio of the same first and second miRNA from human subjects determined not to be suffering from PTSD, wherein an increase or decrease in the ratio for the sample from the human subject against ratio of the same first and second miRNA from human subjects determined not to be suffering from PTSD is indicative that the human subject may be suffering from PTSD.

In one aspect, said miRNA is selected from the group consisting of miR-142-3p, miR-518e, miR-181a, miR-20a, miR-672, miR-29a, miR-130a, miR-29c, miR-220, miR-484, miR-433, miR-337-5p, miR-486-5p, and miR-518f-3p.

The term "diagnosing" includes making diagnostic or prognostic determinations or predictions of disease. In some instances, "diagnosing" includes identifying whether a subject has a disease such as PTSD. Additionally, "diagnosing" includes distinguishing patients with mild PTSD from patients having severe PTSD. In other circumstances, "diagnosing" includes determining the stage or aggressiveness of a disease state, or determining an appropriate treatment method for PTSD.

The nucleotide sequence of the miRNAs herein disclosed may be obtained from the world wide web at www.mirbase.org.

In some embodiments, the methods of the present disclosure use miRNA as markers for PTSD. In some embodiments, miRNA that are present at elevated levels in a biological sample (e.g. serum, plasma, or cerebrospinal fluid) from a subject with PTSD are used as markers. In other embodiments, miRNA that have reduced levels are used as markers. In some embodiments, more than one miRNA from the biological sample may be used as markers. When more than one miRNA biomarker is used, the miRNA may all have elevated levels, all have reduced levels, or a mixture of miRNA with elevated and reduced levels may be used. In some embodiments, the levels of different miRNA from a sample can be processed according to a preset algorithm (e.g. calculating a ratio) before being compared to the miRNA levels from another sample processed with the same or a different algorithm.

The term "an increase or decrease in the levels of the one or more miRNA" refers to an increase or decrease in the amount of a miRNA in a biological sample from a subject compared to the amount of the miRNA in the biological sample from a cohort or cohorts that do not have the PTSD that the subject is being tested for. For instance, increased or decreased levels of miRNA in the biological sample may indicate presence or prognosis for the PTSD. In additional embodiments, certain miRNA may be present in increased or decreased levels in samples taken from different time points from subjects with PTSD or control. In some embodiments, the level of the miRNA marker will be compared to a control to determine whether the level is decreased or increased. The control may be, for example, miRNA in a biological sample from a subject known to be free of PTSD. In other embodiments, the control may be miRNA from a serum sample, a plasma sample, a CSF sample, a tissue sample or a known amount of a synthetic RNA. In additional embodiments, the control may be miRNA in a biological sample from the same subject at a different time. In some embodiments, the increase or decrease in the levels of the one or more miRNA is evaluated by having a p value of less than a specific value in a statistical test, such as but not limited to a T test, an F test, a correlation and regression test, and an analysis of variance (ANOVA) test. In some embodiments, the specific value of which the p value is less than is 0.2, 0.1, 0.05, 0.02, 0.01, 0.005, or 0.001.

In one aspect, said miRNA is selected from the group consisting of miR-142-3p (SEQ ID NO: 1), miR-518e (SEQ ID NO: 2), miR-181a (SEQ ID NO: 3), miR-20a (SEQ ID NO: 4), miR-672 (SEQ ID NO: 5), miR-29a (SEQ ID NO: 6), miR-130a (SEQ ID NO: 7), miR-29c (SEQ ID NO: 8), miR-220 (SEQ ID NO: 9), miR-484 (SEQ ID NO: 10), miR-433 (SEQ ID NO: 11), miR-337-5p (SEQ ID NO: 12), miR-486-5p (SEQ ID NO: 13), and miR-518f-3p (SEQ ID NO: 14). These miRNA have increased or decreased levels in plasma or CSF from patients with PTSD. These miRNA may be used to diagnose PTSD. In addition, these miRNA may be used to predict the progression of PTSD. In another aspect, one or more of these miRNA is selected from the group consisting of miR-142-3p, miR-518e, miR-181a, and miR-20a. The levels of these miRNA may be affected in samples taken from subjects at a specific time and the miRNA levels of the human subject are compared to miRNA levels from samples taken at the same time from subjects determined not to be suffering from PTSD. For example, the levels of these miRNA may be affected in samples taken from subjects at around both 2 AM and 9 AM and the miRNA levels of the human subject are compared to miRNA levels from samples taken at the same time from subjects determined not to be suffering from PTSD. In addition, the specific time is when the subject is asleep or when the subject is awake. In another aspect, said one or more miRNA is selected from the group consisting of miR-672, miR-29a, miR-130a, and miR-29c. The levels of these miRNA may be affected in sample taken from subjects at around 2 AM. In another aspect, said one or more miRNA is selected from the group consisting of miR-220, miR-484, miR-433, and miR-337-5p. The levels of these miRNA may be affected in a sample taken from a subject at around 9 AM. In another aspect, said one or more miRNA is selected from the group consisting of miR-486-5p and miR-518f-3p. The levels of these miRNA may be affected in sample taken from subjects at around 9 AM.

In one aspect, said one or more miRNA is selected from the group consisting of miR-142-3p, miR-518e, miR-181a, miR-20a, miR-672, miR-29a, miR-130a, miR-29c, miR-220, miR-484, miR-433, and miR-337-5p. The levels of these miRNA are measured in a plasma sample. In another aspect, said one or more miRNA is selected from the group consisting of miR-486-5p and miR-518f-3p. The levels of these miRNA are also measured in CSF samples.

In one aspect, the subject is human. In another aspect, the subject is a human and the methods relate to a human suspected of suffering from PTSD. In another aspect, the biological samples described herein include, but is not limited to, blood, plasma, serum, urine, sputum, cerebrospinal fluid (CSF), and ductal fluid samples. In some embodiments, the biological sample is a serum, plasma and/or CSF sample. Serum is typically the fluid, non-cellular portion of coagulated blood. Plasma is also a non-cellular blood sample, but unlike serum, plasma contains clotting factors. In some embodiments, serum, plasma or CSF samples may be obtained from a human subject previously screened for PTSD using other diagnostic methods. Additional embodiments include measuring miRNA in samples from subjects previously or currently undergoing treatment for PTSD. The volume of plasma, serum or CSF obtained and used in the methods described herein may be varied depending upon clinical intent.

One of skill in the art may recognize that many methods exist for obtaining and preparing serum, plasma or CSF samples.

Before performing the methods according to the present disclosure, RNA may be extracted from serum, plasma or CSF and purified using methods known in the art. Many methods are known for isolating total RNA, or to specifically extract small RNA, including miRNA. The RNA may be extracted using commercially-available kits (e.g., Perfect RNA Total RNA Isolation Kit, Five Prime-Three Prime, Inc.; mirVana™ kits, Ambion, Inc.). Alternatively, RNA extraction methods previously published for the extraction of mammalian intracellular RNA or viral RNA may be adapted, either as published or with modification, for extraction of RNA from plasma and serum. RNA may be extracted from plasma or serum using silica particles, glass beads, or diatoms, as in the method or adaptations described in U.S. Publication No. 2008/0057502.

In another aspect, the levels of one or more specific micro RNA are determined by a real time PCR. In some embodiments, the methods of the present disclosure comprise amplifying the miRNA.

Many methods of measuring the levels or amounts of miRNA are contemplated. Any reliable, sensitive, and specific method may be used. In some embodiments, a miRNA is amplified prior to measurement. In other embodiments, the level of miRNA is measured during the amplification process. In still other methods, the miRNA is not amplified prior to measurement.

Many methods exist for amplifying miRNA nucleic acid sequences such as mature miRNA, primary miRNA and precursor miRNA. Suitable nucleic acid polymerization and amplification techniques include reverse transcription polymerase chain reaction (RT-PCR), real-time PCR (quantitative PCR (q-PCR)), nucleic acid sequence-base amplification (NASBA), ligase chain reaction, multiplex ligatable probe amplification, invader technology (Third Wave), rolling circle amplification, in vitro transcription (IVT), strand displacement amplification, transcription-mediated amplification (TMA), RNA (Eberwine) amplification, and other methods that are known to persons skilled in the art. In certain embodiments, more than one amplification method is used, such as reverse transcription followed by real time quantitative PCR (qRT-PCR) (Chen, Nucleic Acids Research, (2005) 33:e179).

A typical PCR reaction includes multiple amplification steps, or cycles that selectively amplify target nucleic acid species: a denaturing step in which a target nucleic acid is denatured; an annealing step in which a set of PCR primers (forward and reverse primers) anneal to complementary DNA strands; and an elongation step in which a thermostable DNA polymerase elongates the primers. By repeating these steps multiple times, a DNA fragment is amplified to produce an amplicon, corresponding to the target DNA sequence. Typical PCR reactions include 20 or more cycles of denaturation, annealing, and elongation. In many cases, the annealing and elongation steps can be performed concurrently, in which case the cycle contains only two steps. Since mature miRNA are single-stranded, a reverse transcription reaction (which produces a complementary cDNA sequence) may be performed prior to PCR reactions. Reverse transcription reactions include the use of, e.g., a RNA-based DNA polymerase (reverse transcriptase) and a primer.

In PCR and q-PCR methods, for example, a set of primers is used for each target sequence. In certain embodiments, the lengths of the primers depends on many factors, including, but not limited to, the desired hybridization temperature between the primers, the target nucleic acid sequence, and the complexity of the different target nucleic acid sequences to be amplified. In certain embodiments, a primer is about 15 to about 35 nucleotides in length. In other embodiments, a primer is equal to or fewer than 15, 20, 25, 30, or 35 nucleotides in length. In additional embodiments, a primer is at least 35 nucleotides in length.

In a further aspect, a forward primer can comprise at least one sequence that anneals to a miRNA biomarker and alternatively can comprise an additional 5' non-complementary region. In another aspect, a reverse primer can be designed to anneal to the complement of a reverse transcribed miRNA. The reverse primer may be independent of the miRNA biomarker sequence, and multiple miRNA biomarkers may be amplified using the same reverse primer. Alternatively, a reverse primer may be specific for a miRNA biomarker.

In some embodiments, two or more miRNA are amplified in a single reaction volume. One aspect includes multiplex q-PCR, such as qRT-PCR, which enables simultaneous amplification and quantification of at least two miRNA of interest in one reaction volume by using more than one pair of primers and/or more than one probe. The primer pairs comprise at least one amplification primer that uniquely binds each miRNA, and the probes are labeled such that they are distinguishable from one another, thus allowing simultaneous quantification of multiple miRNA. Multiplex qRT-PCR has research and diagnostic uses, including but not limited to detection of miRNA for diagnostic, prognostic, and therapeutic applications.

The qRT-PCR reaction may further be combined with the reverse transcription reaction by including both a reverse transcriptase and a DNA-based thermostable DNA polymerase. When two polymerases are used, a "hot start" approach may be used to maximize assay performance (U.S. Pat. Nos. 5,411,876 and 5,985,619). For example, the components for a reverse transcriptase reaction and a PCR reaction may be sequestered using one or more thermoactivation methods or chemical alteration to improve polymerization efficiency (U.S. Pat. Nos. 5,550,044; 5,413,924 and 6,403,341).

In some embodiments, a kit can be used for detecting or diagnosing post traumatic stress disorder (PTSD) in a human subject suspected of having PTSD. The kit may comprise one or more polynucleotide molecules that hybridize to one or more miRNAs, wherein each of the polynucleotide molecules has at least about 80%, 85%, 86%, 87%, 88%, 89%, 90%, 91%, 92%, 93%, 94%, 95%, 96%, 97%, 98% or 99% sequence identity to a complementary sequence to the one or more miRNAs selected from the group consisting of miR-142-3p, miR-518e, miR-181a, miR-20a, miR-672, miR-29a, miR-130a, miR-29c, miR-220, miR-484, miR-433, miR-337-5p, miR-486-5p, and miR-518f-3p. In one specific embodiment, kit may comprise one or more polynucleotide molecules that hybridize to one or more miRNAs, wherein each of the polynucleotide molecules has 100% sequence identity to a complementary sequence to the one or more miRNAs selected from the group consisting of miR-142-3p, miR-518e, miR-181a, miR-20a, miR-672, miR-29a, miR-130a, miR-29c, miR-220, miR-484, miR-433, miR-337-5p, miR-486-5p, and miR-518f-3p. In one embodiment, the kit comprises at least two polynucleotide molecules where each of which hybridizes to a different miRNA, wherein each of the polynucleotide molecules has at least about 80%, 85%, 86%, 87%, 88%, 89%, 90%, 91%, 92%, 93%, 94%, 95%, 96%, 97%, 98% or 99% sequence identity to a complementary sequence to the one or more miRNAs selected from the group consisting of miR-142-3p, miR-518e, miR-181a, miR-20a, miR-672, miR-29a, miR-130a, miR-29c, miR-220, miR-484, miR-433, miR-337-5p, miR-486-5p, and miR-518f-3p. In one specific embodiment, the kit may comprise at least two polynucleotide molecules that hybridize to different miRNAs, wherein each of the polynucleotide molecules has 100% sequence identity to a complementary sequence to the one or more miRNAs selected from the group consisting of miR-142-3p, miR-518e, miR-181a, miR-20a, miR-672, miR-29a, miR-130a, miR-29c, miR-220, miR-484, miR-433, miR-337-5p, miR-486-5p, and miR-518f-3p. In some embodiments, the polynucleotide molecules are labeled and/or immobilized onto a solid substrate.

As used herein, "identity" is a measure of the identity of nucleotide sequences compared to a reference nucleotide sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there are several methods to measure identity between two polynucleotide sequences, the term "identity" is well known to skilled artisans (Carillo, H. & Upton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), BLASTP, ExPASy, BLASTN, FASTA (Atschul, S. F., et al., J Molec Biol 215:403 (1990)) and FASTDB. Examples of methods to determine identity and similarity are discussed in Michaels, G. and Garian, R., Current Protocols in Protein Science, Vol 1, John Wiley & Sons, Inc. (2000), which is incorporated by reference.

If the reference sequence is shorter or longer than the query sequence because of 5' terminus or 3' terminus additions or deletions, but not because of internal additions or deletions, a manual correction can be made, because the FASTA program does not account for 5' terminus and 3' terminus truncations or additions of the reference sequence when calculating percent identity. For query sequences truncated at the 5' or 3' termini, relative to the reference sequence, the percent identity is corrected by calculating the number of nucleotides of the query sequence that are 5' and/or 3' terminus to the reference sequence that are not matched/aligned, as a percent of the total bases of the query sequence. The results of the FASTA sequence alignment determine matching/alignment. The alignment percentage is then subtracted from the percent identity, calculated by, for example, FASTA program using specified parameters, to arrive at a final percent identity score. This corrected score can be used for the purposes of determining how alignments "correspond" to each other, as well as percentage identity. Nucleotides of the reference sequence that extend past the 5' or 3' termini of the query sequence may be considered for the purposes of manually adjusting the percent identity score. That is, nucleotides that are not matched/aligned with the 5' or 3' termini of the comparison sequence may be counted when manually adjusting the percent identity score or alignment numbering.

For example, a 90 nucleotide query sequence is aligned with a 100 nucleotide reference sequence to determine percent identity. The deletion occurs at the 5' terminus of the query sequence and therefore, the FASTA alignment does not show a match/alignment of the first 10 nucleotides at the 5' terminus. The 10 unpaired nucleotides represent 10% of the reference sequence (number of nucleotides at the 5' and 3' termini not matched/total number of nucleotides in the reference sequence) so 10% is subtracted from the percent identity score calculated by the FASTA program. If the remaining 90 nucleotides were perfectly matched (100% alignment) the final percent identity would be 90% (100% alignment–10% unmatched overhang). In another example, a 90 nucleotide query sequence is compared with a 100 nucleotide reference sequence, except that the deletions are internal deletions. In this case the percent identity calculated by FASTA is not manually corrected, since there are no nucleotides at the 5' or 3' termini of the subject sequence that are not matched/aligned with the query. In still another example, a 110 polynucleotide query sequence is aligned with a 100 nucleotide reference sequence to determine percent identity. The addition in the query occurs at the 5' terminus of the query sequence and therefore, the FASTA alignment may not show a match/alignment of the first 10 nucleotides at the 5' terminus. If the remaining 100 nucleotides of the query sequence have 95% identity to the entire length of the reference sequence, the 5' terminal addition of the query would be ignored and the percent identity of the query to the reference sequence would be 95%.

In certain embodiments, labels, dyes, or labeled probes and/or primers are used to detect amplified or unamplified miRNA. The skilled artisan will recognize which detection methods are appropriate based on the sensitivity of the detection method and the abundance of the target. Depending on the sensitivity of the detection method and the abundance of the target, amplification may or may not be required prior to detection. One skilled in the art will recognize the detection methods where miRNA amplification is preferred.

A probe or primer may include Watson-Crick bases or modified bases. Modified bases include, but are not limited to, the AEGIS bases (from Eragen Biosciences), which have been described, e.g., in U.S. Pat. Nos. 5,432,272; 5,965,364 and 6,001,983. In certain aspects, bases are joined by a natural phosphodiester bond or a different chemical linkage. Different chemical linkages include, but are not limited to, a peptide bond or a Locked Nucleic Acid (LNA) linkage, which is described, e.g., in U.S. Pat. No. 7,060,809.

In a further aspect, oligonucleotide probes or primers present in an amplification reaction are suitable for monitoring the amount of amplification product produced as a function of time. In certain aspects, probes having different single stranded versus double stranded character are used to detect the nucleic acid. Probes include, but are not limited to, the 5'-exonuclease assay (e.g. TaqMan™) probes (see U.S. Pat. No. 5,538,848), stem-loop molecular beacons (see, e.g. U.S. Pat. Nos. 6,103,476 and 5,925,517), stemless or linear beacons (see, e.g. WO 9921881, U.S. Pat. Nos. 6,485,901 and 6,649,349), peptide nucleic acid (PNA) Molecular Beacons (see, e.g. U.S. Pat. Nos. 6,355,421 and 6,593,091), linear PNA beacons (see, e.g. U.S. Pat. No. 6,329,144), non-FRET probes (see, e.g. U.S. Pat. No. 6,150,097), Sunrise™/AmplifluorB™ probes (see, e.g. U.S. Pat. No. 6,548,250), stem-loop and duplex Scorpion™ probes (see, e.g. U.S. Pat. No. 6,589,743), bulge loop probes (see, e.g. U.S. Pat. No. 6,590,091), pseudo knot probes (see, e.g. U.S. Pat. No. 6,548,250), cyclicons (see, e.g. U.S. Pat. No. 6,383,752), MGB Eclipse™ probe (Epoch Biosciences), hairpin probes (see, e.g., U.S. Pat. No. 6,596,490), PNA light-up probes, antiprimer quench probes (Li, Clin. Chem. (2006) 53:624-633), self-assembled nanoparticle probes, and ferrocene-modified probes described, for example, in U.S. Pat. No. 6,485,901.

In certain embodiments, one or more of the primers in an amplification reaction can include a label. In some embodiments, different probes or primers comprise detectable labels that are distinguishable from one another. In some embodiments a nucleic acid, such as the probe or primer, may be labeled with two or more distinguishable labels.

In some aspects, a label is attached to one or more probes and has one or more of the following properties: (i) provides a detectable signal; (ii) interacts with a second label to modify the detectable signal provided by the second label, e.g., FRET (Fluorescent Resonance Energy Transfer); (iii) stabilizes hybridization, e.g., duplex formation; and (iv) provides a member of a binding complex or affinity set, e.g., affinity, antibody-antigen, ionic complexes, hapten-ligand (e.g., biotin-avidin). In still other aspects, use of labels can be accomplished using any one of a large number of known techniques employing known labels, linkages, linking groups, reagents, reaction conditions, and analysis and purification methods.

miRNA can be detected by direct or indirect methods. In a direct detection method, one or more miRNA are detected by a detectable label that is linked to a nucleic acid molecule. In such methods, the miRNA may be labeled prior to binding to the probe. Therefore, binding is detected by screening for the labeled miRNA that is bound to the probe. The probe is optionally linked to a bead in the reaction volume.

In certain embodiments, nucleic acids are detected by direct binding with a labeled probe, and the probe is subsequently detected. In one embodiment of the present disclosure, the nucleic acids, such as amplified miRNA, are detected using FlexMAP Microspheres (Luminex) conjugated with probes to capture the desired nucleic acids.

Some methods may involve detection with polynucleotide probes modified with fluorescent labels or branched DNA (bDNA) detection, for example.

In some embodiments, PTSD may be detected or diagnosed comprising methods of detecting an miRNA or plurality of miRNAs in a biological sample. Such methods may utilize probes with an adjusted sensitivity such that specific miRNA is only detected in samples from subjects suffering from PTSD. The methods comprise contacting a first biological sample, taken from a subject suspected of having a PTSD, with a probe for binding at least one miRNA selected from the group consisting of miR-142-3p, miR-518e, miR-181a, miR-20a, miR-672, miR-29a, miR-130a, miR-29c, miR-220, miR-484, miR-433, miR-337-5p, miR-486-5p, and miR-518f-3p, to produce an miRNA-probe complex. The miRNA-probe complex is then detected by Northern Blot Analysis or a real-time PCR. The absence of the miRNA-probe complex is indicative of the absence of the microRNA in the first biological sample. In one embodiment, the probe is detectably labeled. In another embodiment, the method further comprises administering a therapeutic to said subject if the presence of the miRNA-probe complex is detected.

In other embodiments, nucleic acids are detected by indirect detection methods. For example, a biotinylated probe may be combined with a stretavidin-conjugated dye to detect the bound nucleic acid. The streptavidin molecule binds a biotin label on amplified miRNA, and the bound miRNA is detected by detecting the dye molecule attached to the streptavidin molecule. In one embodiment, the streptavidin-conjugated dye molecule comprises Phycolink® Streptavidin R-Phycoerythrin (PROzyme). Other conjugated dye molecules are known to persons skilled in the art.

Labels include, but are not limited to: light-emitting, light-scattering, and light-absorbing compounds which generate or quench a detectable fluorescent, chemiluminescent, or bioluminescent signal (see, e.g. Kricka, Nonisotopic DNA Probe Techniques, Academic Press, San Diego (1992) and Garman, Non-Radioactive Labeling, Academic Press (1997)). Fluorescent reporter dyes useful as labels include, but are not limited to, fluoresceins (see, e.g. U.S. Pat. Nos. 5,188,934, 6,008,379, and 6,020,481), rhodamines (see, e.g. U.S. Pat. Nos. 5,366,860; 5,847,162; 5,936,087; 6,051,719 and 6,191,278), benzophenoxazines (see, e.g. U.S. Pat. No. 6,140,500), energy-transfer fluorescent dyes, comprising pairs of donors and acceptors (see, e.g. U.S. Pat. Nos. 5,863,727; 5,800,996 and 5,945,526), and cyanines (see, e.g. WO 9745539), lissamine, phycoerythrin, Cy2, Cy3, Cy3.5, Cy5, Cy5.5, Cy7, FluorX (Amersham), Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, Tetramethylrhodamine, and/or Texas Red, as well as any other fluorescent moiety capable of generating a detectable signal. Examples of fluorescein dyes include, but are not limited to, 6-carboxyfluorescein; 2',4',1,4,-tetrachlorofluorescein, and 2',4',5',7',1,4-hexachlorofluorescein. In certain aspects, the fluorescent label is selected from SYBR-Green, 6-carboxyfluorescein ("FAM"), TET, ROX, VICTM, and JOE. For example, in certain embodiments, labels are different fluorophores capable of emitting light at different, spectrally-resolvable wavelengths (e.g., 4-differently colored fluorophores); certain such labeled probes are known in the art and described above, and in U.S. Pat. No. 6,140,054. A dual labeled fluorescent probe that includes a reporter fluorophore and a quencher fluorophore is used in some embodiments. It will be appreciated that pairs of fluorophores are chosen that have distinct emission spectra so that they can be easily distinguished.

In still a further aspect, labels are hybridization-stabilizing moieties which serve to enhance, stabilize, or influence hybridization of duplexes, e.g., intercalators and intercalating dyes (including, but not limited to, ethidium bromide and SYBR-Green), minor-groove binders, and cross-linking functional groups (see, e.g. Blackburn, "DNA and RNA Structure" in Nucleic Acids in Chemistry and Biology (1996)).

In further aspects, methods relying on hybridization and/or ligation to quantify miRNA may be used, including oligonucleotide ligation (OLA) methods and methods that allow a distinguishable probe that hybridizes to the target nucleic acid sequence to be separated from an unbound probe. As an example, HARP-like probes, as disclosed in U.S. Patent Publication No. 20060078894 may be used to measure the amount of miRNA. In such methods, after hybridization between a probe and the targeted nucleic acid, the probe is modified to distinguish the hybridized probe from the unhybridized probe. Thereafter, the probe may be amplified and/or detected. In general, a probe inactivation region comprises a subset of nucleotides within the target hybridization region of the probe. To reduce or prevent amplification or detection of a HARP probe that is not hybridized to its target nucleic acid, and thus allow detection of the target nucleic acid, a post-hybridization probe inactivation step is carried out using an agent which is able to distinguish between a HARP probe that is hybridized to its targeted nucleic acid sequence and the corresponding unhybridized HARP probe. The agent is able to inactivate or modify the unhybridized HARP probe such that it cannot be amplified.

In an additional embodiment of the method, a probe ligation reaction may be used to quantify miRNA. In a Multiplex Ligation-dependent Probe Amplification (MLPA) technique (Schouten, Nucleic Acids Research (2002) 30:e57), pairs of probes which hybridize immediately adjacent to each other on the target nucleic acid are ligated to each other only in the presence of the target nucleic acid. In some aspects, MLPA probes have flanking PCR primer binding sites. MLPA probes can only be amplified if they have been ligated, thus allowing for detection and quantification of miRNA biomarkers.

EXAMPLES

The following examples illustrate various embodiments of the present disclosure and are not intended to limit the scope of the invention.

Patients included thirteen medication-free outpatients with chronic civilian PTSD, and eleven approximately age, sex and BMI-matched, non-traumatized, healthy subjects (median age 29.5 years old, 5 women, 5 men). Patients were otherwise physically healthy, with no psychotropic medication for at least three weeks prior to lumbar puncture and concomitant venipuncture, and did not meet criteria for alcohol or substance abuse, or dependence, for at least six months prior to the study. However, the required medication-free period for PTSD patients was extended to six weeks for patients previously taking fluoxetine or other serotonin reuptake inhibitors (SSRI's). Patients were drug-free for at least 8 weeks before sampling.

Psychiatric diagnoses were established using the Structured Clinical Interview for DSM-IV (SCID). The severity of PTSD was determined using the Clinician-Administered PTSD Scale (CAPS). Severity of depressive, anxiety and overall symptoms was assessed using the Inventory of Depressive Symptomatology (IDS), Hamilton Anxiety Rating Scale (HAMA) and Clinical Global Impression—Severity scale (CGI-S), respectively. Individuals with PTSD and controls did not differ with regard to age, gender distribution, race, or body mass index (BMI). Severity of PTSD was moderate, with a CAPS score of 73.1±10.3. Depression (IDS 16.4±8.2), Anxiety (HAMA 13.1±6.8) and overall symptom severity levels (CGI-S 4±1.2) were moderate as well.

Plasma collection: Blood samples were collected from PTSD and Healthy Control patients. The patients were studied at the National Institutes of Health, under an IRB approved protocol. For this study, patients were chronically implanted with indwelling intravenous catheters, and blood collected each hour, over a 27 hour period. There were at least two 9 AM time points in this entire collection, and samples from second 9 AM time point was chosen for analysis. The 2 AM time point was chosen as the time point immediately preceding the 9 AM time point. Care was taken to ensure that blood samples, drawn by hand from the indwelling catheter, were immediately anti-coagulated with sodium citrate, and plasma collected by centrifugation. Care was taken to ensure that the 2 AM sampling was done without disturbing the patient, should that patient be asleep. Following immediate centrifugation, the supernatant solutions were aliquoted and stored frozen at −80° C., and reserved for later analysis. For this study, plasma samples collected at 2 AM and 9 AM were used.

Lumbar puncture (LP) was performed between 8:00 and 9:00 AM by an experienced physician. A 20-gauge introducer needle was inserted and approximately 15 cc of CSF was withdrawn, centrifuged at 4,000 RPM, and frozen in aliquots at −80° C. for later assay. The LPs were drawn at a different time than the 27 hour study described above.

RNA was isolated by standard methods from plasma and CSF, and subjected to analysis using the TaqMan kit (Invitrogen/Thermo). Analysis was performed by ratio'ing signals to an internal standard. Accurate data points were characterized on the basis of reproducible technical replicates, low % coefficient of variation (CV<5%), present within the linear portion of the standard curve, and a value less than 40 cycles.

Experiments were conducted for the identification of PTSD-specific microRNA in plasma that distinguish PTSD from healthy control patients at both 2 AM and 9 AM.

Table 1 lists the top four microRNA that distinguish plasma from PTSD patients relative to plasma isolated from healthy controls, and that are also significantly different in collections performed at both 2 AM and 9 AM. The microRNA, miR-142-3p, miR-181a and miR-20a, are elevated in the range of 5-15 fold at 2 AM, while miR-518e was reduced by 150-fold. By contrast, at 9 AM, all four miR's are profoundly elevated. microRNA, miR-518e, miR-181a, and miR-20a are elevated ca. 20-60-fold, while miR-142-3p was significantly elevated by a remarkable 183-fold. There were three microRNA that were significantly elevated in a PTSD-specific manner at both 2 AM and 9 AM, and one miRNA (miR-518e) that was significantly reduced at 2 AM, but elevated at 9 AM.

TABLE 1

Time-of-Day Dependence of microRNA in Plasma of PTSD and Control Patients: PTSD-Specificity at 2 AM and 9 AM.

| MicroRNA | 2 AM PTSD/HC | 2 AM P-value | 9 AM PTSD/HC | 9 AM P-value |
|---|---|---|---|---|
| miR-142-3p | ↑12 | 0.004 | ↑183 | 0.05 |
| miR-518e | ↓150 | 0.02 | ↑24 | 0.03 |
| miR-181a | ↑6.8 | 0.01 | ↑58 | <0.001 |
| miR-20a | ↑4.6 | 0.03 | ↑55 | 0.03 |

Possibly of relevance to PTSD is the fact that miR-518e is not only brain-enriched, and has also been implicated in neuronal survival. This is the type of potential defect that could be treated with a microRNA mimic, administered at bedtime. Mimics are either mature microRNA, or double stranded pre-miRs, both of which can be administered as drugs, either by mouth or IV. MiR-181a is brain enriched, and is associated with neuronal survival.

Identification of PTSD-specific microRNA in plasma that distinguish PTSD from healthy control patients at 2 AM but not 9 AM.

Table 2 lists the top four microRNA that distinguish plasma from PTSD patients relative to plasma isolated from healthy controls, and that are also significantly different in collections taken at 2 AM, but not 9 AM. These were miR-672, miR-29a, miR-130a, and miR-29c. MicroRNA-672 showed the most significant (P=0.001) change and the highest fold difference (248-fold elevated). The data in the 9 AM columns indicate that plasma levels of all four of these microRNA are statistically identical. Importantly, it does not mean that they are individually "zero". It only means that the ratio of levels in plasma from PTSD and Healthy Control patients are close to being identical.

TABLE 2 time-of-Day Dependence of microRNA in Plasma of PTSD and Control Patients: PTSD-Specificity at 2 AM but not 9 AM.

| MicroRNA | 2 AM | | 9 AM | |
|---|---|---|---|---|
| | PTSD/HC | P-value | PTSD/HC | P-value |
| miR-672 | ↑248 | 0.001 | ca.1.1 | 0.98 |
| miR-29a | ↑90 | 0.01 | ↑3.1 | 0.34 |
| Mir-130a | ↑32 | 0.002 | ↓36 | 0.19 |
| miR-29c | ↑28 | 0.003 | ↓38 | 0.04 |

Possibly of relevance to PTSD is the fact that miR-29a is associated with neuronal survival.

Identification of PTSD-specific microRNA in plasma that distinguish PTSD from healthy control patients at 9 AM but not 2 AM.

Table 3 lists the top four microRNA that distinguish plasma from PTSD patients relative to plasma isolated from healthy controls, and that are also significantly different in collections taken at 9 AM, but not 2 AM. These are miR-220, miR-484, miR-433, and miR-337-5p. MicroRNA-220 had the highest fold difference (944-fold elevated), and was one of two miRs (miR-433 being the other) with a P value of 0.01. The data in the 2 AM columns indicate that plasma levels of all four of these microRNA are statistically identical. However, miR-337-p at 2 AM trends towards significance, and the others are still somewhat elevated, although with P values substantially greater than 0.05.

TABLE 3

Time-of-Day Dependence of microRNA in Plasma of PTSD and Control Patients: PTSD-Specificity at 9 AM but not 2 AM.

| MicroRNA | 2 AM | | 9 AM | |
|---|---|---|---|---|
| | PTSD/HC | P-value | PTSD/HC | P-value |
| miR-220 | ↑8 | 0.17 | ↑944 | 0.01 |
| miR-484 | ↑5.4 | 0.12 | ↑294 | 0.05 |
| miR-433 | ↑1.5 | 0.86 | ↑51 | 0.01 |
| miR-337-5p | ↑35 | 0.08 | ↓38 | 0.04 |

Perhaps relevantly, miR-220 targets several genes associated with schizophrenia (viz.bioinfo.mc.vanderbilt.edu/SZGR/displavGenePaqe.do?qeneid=10048), including RANBP9 (RAN binding protein 9), and others.

Identification of PTSD-specific microRNA in CSF that distinguish PTSD from healthy control patients at 9 AM.

Table 4 lists the top two microRNA that distinguish cerebrospinal fluid (CSF) from PTSD patients relative to CSF isolated from healthy controls, in collections taken only at 9 AM These are miR-486-5p and miR-518f-3p. The miR-486-5p was elevated 105-fold, and was significant only in males with PTSD. By contrast, miR-518f-3p was significantly reduced by ca. 1450-fold, and equally in both males and females with PTSD. The significance is exceptional (P=0.006).

TABLE 4

PTSD-Specific MicroRNA distinguish between CSF from PTSD and Healthy Controls in samples taken at 9 AM

| MicroRNA | Male: PTSD/HC | P value |
|---|---|---|
| miR-486-5p | ↑105 (male only) | 0.004 |
| miR-518f-3p | ↓1449 (M = F) | 0.006 |

The change of miR-486-5p expression is gender dependent. Clinically, PTSD in the civilian population manifests itself more frequently in females than in males, especially in the low-comorbidity population. The gender independent miR-518f-3p is remarkable in that it affects the expression of mRNA associated with multiple neurological disease processes, such as Huntington's Disease. miR-518f-3p has ALS (amyotrophic lateral sclerosis, VAPN gene), Alzheimer-disease (PRDX6 gene), cerebro-amygdalar fear signaling (RAP1B gene), brain aging, and cognitive decline (TOLLIP gene), and Myosin-X, a negative regulator of cortical axon growth.

A composite biomarker ratio is a statistically more compelling biomarker than any one of the individual biomarkers.

FIG. 1 shows that the ratio of [miR-181a/miR-337-5p] distinguishes PTSD plasma from Healthy Control plasma, with a dynamic range of ca. 2200-fold. The P value (0.0006) and the ROC AUC of 0.98 is better that either independently. Other ratio's approach these qualities of range and significance.

The approach of ratio'ing a disease-specific elevated biomarker to a disease-specific reduced biomarker has the effect of extending the range, and significance of the assay, and also of decreasing both false positives and false negatives.

Individual miRNAs may be highly specific PTSD-specific biomarkers: Specific miRNAs may individually serve as PTSD-specific biomarkers in plasma and cerebrospinal fluid from well-defined, low comorbidity PTSD patients. These patients may specifically lack major depressive disorder (MDD) and substance abuse. Nonetheless, they may be behaviorally benefited by treatment with SSRI's, including paroxetine. The data suggest that the levels of PTSD-specific miRNAs may depend on the time of day the samples are taken. MiRNA expression levels at 2 AM versus 9 AM were examined to yield insights regarding diurnal rhythm. In the 9 AM datasets, there are both elevations and reductions in PTSD versus Healthy Controls. This is relevant to use as a biomarker in the general clinical setting, because few patients (or caregivers) are available at 2 AM.

The diagnostic assay for PTSD may be optimized by stratification of two miRNAs: By calculating the ratio of a significantly elevated miRNA, to a miRNA that is significantly reduced, the dynamic range of the assay may be substantially increased, and the statistical significance concomitantly enhanced as well. In the example shown by FIG. 1, the ratios of miR-181a to miR-337-5p were calculated. The dynamic range was extended to more than 3 logs (base 10), and the P value was reduced to 0.0006. Importantly the Receiver Operating Condition (ROC) curve generated an area-under-the-curve (AUC) value of 0.98, indicating a nearly perfect elimination of both false positives and false negatives. Another advantage of this ratio method for generating a diagnostic metric may be that by dividing two identical measurements, the units cancel out, and the resulting metric no longer depends on how the original quantities were calculated. It should also be noted that the results may be optimized by algorithms in addition to ratio'ing levels of miRNA.

Biomarkers for PTSD may yield information on different aspects of the disease: Multiple miRNA may vary in their levels of PTSD-specific expression. It may be possible that different miRNA may independently yield information on different aspects of the disease.

MiRNA may be used as biomarkers for risk of developing PTSD. For example, risk may be increased when the dorsal anterior cingulate cortex (dACC) and the amygdala are intrinsically hyperactivated. This is the basis of the hyperarousal symptom. It is therefore possible that these parts of the brain may be related to specific miRNAs, and that activation may have consequences for miRNA expression. In parallel, we also know that in PTSD, the circuit between the vmPFC ("area 25") and the hippocampus is degraded. This results in inability to use executive function in the frontal cortex to suppress the fear response in the limbic system. It may be possible that the failure of the vmPFC/hippocampus circuit could have specific consequences in terms of specific changes in miRNA biomarkers in the plasma.

MiRNA may be used as biomarkers for choice of treatment: Conventionally, treatment for PTSD consists of selective serotonin reuptake inhibitors (SSRI's) and cognitive behavior therapy (CBT). There are other types of therapy when neither of these seems to work. It may be possible that certain of the miRNAs may yield information of which of the two will work. Alternatively, information from miRNA biomarkers may indicate that neither will work, and that something else needs to be deployed.

miRNA as biomarkers for PTSD progression and/or response to treatment: In place of a subjective clinical opinion by either the patient or the therapist, it may possible that some of the identified miRNA may be used as a timely indicator of PTSD progression and/or response to therapy.

In the case of anti-depressants, sometimes months are needed before symptoms appear to be reduced in severity. A biomarker for response might be used to herald either success, or warn that valuable time is being lost by sustaining use of a therapy that will eventually be shown not to work.

miRNA as biomarkers for recovery: The goal of therapy for PTSD is for the patient to escape from the host of symptoms associated with the disorder. The consequences of therapy may beto return the patient to a "healthy control" condition. Alternatively, the therapy may enhance resilience while leaving the fundamental problems in place. A biomarker for recovery may yield information on both of these possibilities.

All references cited herein are incorporated herein by reference in their entirety. To the extent publications and patents or patent applications incorporated by reference contradict the disclosure contained in the specification; the specification will supersede any contradictory material.

What is claimed is:

1. A method of detecting microRNA (miRNA) miR-142-3p, miR-181a and miR-20a levels in a human subject suspected of having post-traumatic stress disorder (PTSD), the method comprising
   (a) obtaining a biological sample isolated from the human subject, and
   (b) measuring the levels of miR-142-3p, miR-181a and miR-20a in the biological sample.

2. The method of claim 1, wherein the biological sample is taken from the human subject at one or more time points.

3. The method of claim 1, further comprising measuring levels of one or more miRNA are selected from the group consisting of miR-518e, miR-672, miR-29a, miR-130a, miR-29c, miR-220, miR-484, miR-433, miR-337-5p, miR-486-5p, and miR-518f-3p in the biological sample.

4. The method of claim 1, wherein the biological sample is taken from the human subject at a specific time, and the miRNA levels of the human subject are compared to miRNA levels from samples taken at the same time from normal human subjects determined not to be suffering from PTSD.

5. The method of claim 4, wherein the specific time is when the human subject is asleep.

6. The method of claim 1, wherein the biological sample is taken from the human subject at 2 AM.

7. The method of claim 1, wherein the biological sample is taken from the human subject at 9 AM.

8. The method of claim 1, further comprising measuring two or more miRNA is selected from the group consisting of miR-518e, miR-672, miR-29a, miR-130a, miR-29c, miR-220, miR-484, miR-433, and miR-337-5p.

9. The method of claim 1, further comprising measuring one or more miRNA is selected from the group consisting of miR-486-5p and miR-518f-3p.

10. The method of claim 1, wherein the levels of the miRNA are determined by real-time PCR.

11. The method of claim 1, wherein the biological sample is a plasma sample.

12. The method claim 1, wherein the biological sample is a cerebrospinal fluid (CSF) sample.

13. The method claim 1, wherein the human subject is male.

14. The method of claim 1, wherein the human subject is female.

* * * * *